United States Patent
Li et al.

(10) Patent No.: US 11,735,321 B2
(45) Date of Patent: Aug. 22, 2023

(54) SYSTEM FOR THE PROGNOSTICS OF THE CHRONIC DISEASES AFTER THE MEDICAL EXAMINATION BASED ON THE MULTI-LABEL LEARNING

(71) Applicant: ZHEJIANG LAB, Hangzhou (CN)

(72) Inventors: Jingsong Li, Hangzhou (CN); Tianshu Zhou, Hangzhou (CN); Chengkai Wu, Hangzhou (CN); Ying Zhang, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 17/543,736

(22) Filed: Dec. 7, 2021

(65) Prior Publication Data

US 2022/0093257 A1 Mar. 24, 2022

Related U.S. Application Data

(63) Continuation of application No. PCT/CN2021/071826, filed on Jan. 14, 2021.

(30) Foreign Application Priority Data

Jan. 14, 2020 (CN) .......................... 202010038223.2

(51) Int. Cl.
*G16H 50/20* (2018.01)
*G16H 10/60* (2018.01)
(Continued)

(52) U.S. Cl.
CPC ............. *G16H 50/20* (2018.01); *G16H 10/60* (2018.01); *A61B 5/7267* (2013.01); *G16H 40/20* (2018.01)

(58) Field of Classification Search
CPC ........ G16H 50/20; G16H 10/60; G16H 40/20; A61B 5/7267; G06N 3/00; G06N 5/00
See application file for complete search history.

(56) References Cited

U.S. PATENT DOCUMENTS

| 2018/0096104 | A1* | 4/2018 | Maley ................... G16H 40/67 |
| 2020/0152184 | A1* | 5/2020 | Steedman Henderson .................. G06F 40/35 |
| 2020/0303075 | A1* | 9/2020 | Krishna ................ G16H 50/30 |

FOREIGN PATENT DOCUMENTS

| CN | 108520780 A | 9/2018 |
| CN | 108648829 A | 10/2018 |

(Continued)

OTHER PUBLICATIONS

R. Ge, R. Zhang and P. Wang, "Prediction of Chronic Diseases With Multi-Label Neural Network," in IEEE Access, vol. 8, pp. 138210-138216 (Year: 2020).*

(Continued)

*Primary Examiner* — Fonya M Long
*Assistant Examiner* — Anthony Balaj
(74) *Attorney, Agent, or Firm* — W&G Law Group

(57) ABSTRACT

Provided is a system for the prognostics of the chronic diseases after the medical examination based on the multi-label learning, including a data acquisition module, a data preprocessing module, a basic predicting model constructing module, and a local predicting module. The data acquisition module is configured to acquire physical examination data of a physical examination user. The basic predicting model constructing module is configured to construct a multi-label learning model for a physical examination scenario. The local predicting module includes a local model training unit and a predicting unit. The local model training unit adjusts the basic predicting model into a local predicting model, and solidifies the local predicting model into the local predicting module. The predicting unit outputs a predicted prognostic index for an occurrence of a plurality of chronic diseases, and finally acquires a future expected occurrence time of the chronic diseases.

2 Claims, 4 Drawing Sheets

(51) Int. Cl.
  *G16H 40/20*   (2018.01)
  *A61B 5/00*    (2006.01)

(56) References Cited

FOREIGN PATENT DOCUMENTS

| CN | 108804718 A  | 11/2018 |
|----|--------------|---------|
| CN | 109036553 A  | 12/2018 |
| CN | 111312401 A  | 6/2020  |
| WO | 2018134682 A1 | 7/2018 |

OTHER PUBLICATIONS

M. Zhang and Z. Zhou, "A Review on Multi-Label Learning Algorithms," in IEEE Transactions on Knowledge and Data Engineering, vol. 26, No. 8, pp. 1819-1837, (Year: 2014).*
Himanshu Jain, Yashoteja Prabhu, and Manik Varma. Extreme Multi-label Loss Functions for Recommendation, Tagging, Ranking & Other Missing Label Applications. In Proceedings of the 22nd ACM SIGKDD International Conference on Knowledge Discovery and Data Mining (KDD '16). 935-944 (Year: 2016).*
International Search Report (PCT/CN2021/071826); dated Apr. 2, 2021.
The Study on Multi-disease Risk Prediction Model Based on Deep Learning; Date of Mailing: Jul. 15, 2019.
A Novel Deep Neural Network Model for Multi-Label Chronic Disease Prediction; Date of Mailing: Apr. 24, 2019.

* cited by examiner

SYSTEM FOR THE PROGNOSTICS OF THE CHRONIC DISEASES AFTER THE MEDICAL EXAMINATION BASED ON THE MULTI-LABEL LEARNING

CROSS-REFERENCE TO RELATED APPLICATIONS

The present application is a continuation of International Application No. PCT/CN2021/071826, filed on Jan. 14, 2021, which claims priority to Chinese Application No. 202010038223.2, filed on Jan. 14, 2020, the contents of both of which are incorporated herein by reference in their entireties.

TECHNICAL FIELD

The present invention belongs to the field of medical treatment and machine learning technologies, and in particular relates to a system for the prognostics of the chronic diseases after the medical examination based on the multi-label learning.

BACKGROUND

Various chronic diseases, including a diabetes, a heart disease, a coronary heart disease, and a chronic kidney disease, have become the most important diseases that have caused a significant decline in a quality of life of people and a substantial increase in a medical economic burden on a global scale. Chronic diseases have features of a high concealment in an early stage, a low awareness rate, a high damage in a later stage, and an extremely low cure rate. According to statistics of the World Health Organization (WHO), the number of deaths caused by cardiovascular diseases and a diabetes in the world was 17 million in 2012, accounting for 50.2% of deaths from non-communicable diseases. In 2015 report on prevention and control of chronic diseases, WHO pointed out that effects of prevention and treatment of chronic diseases on a global scale were significantly lower than expected.

Early awareness and early warning are of great significance to the prevention and treatment of chronic diseases. Chronic diseases can generally be prevented by controlling work and rest, diets, exercise and other methods after early warning. However, once a patient has experienced organic lesions, the diseases can hardly be truly cured. Another difficulty in the prevention and treatment of chronic diseases is that various diseases often occur concurrently. According to a review report of 35 studies compiled by Lehnert et al. in 2011, the number of chronic diseases (MCCs) of an individual was positively or exponentially correlated to costs of diagnosis and treatment. Therefore, under a premise that a small number of chronic diseases or related abnormal physiological indicators are known, predicting an occurrence of other chronic diseases and carrying out effective interventions are of great significance to improve a control effect of chronic diseases and greatly reduce a medical burden.

Medical examination is a medical method that can be performed by both healthy and unhealthy people, and has a good prospective ability to predict the occurrence of chronic diseases. However, a current medical examination system mainly determines whether a patient has a specific disease at a current time based on current examination indicators and has a lack of systematic technical means to perform prognosis of the occurrence of chronic diseases in the next several years via current examination data and an existing chronic disease state of a medical examinee.

A medical examination clinical decision support system in the prior art that predicts various diseases with a traditional single-label machine learning method cannot extract a concurrent correlation between different chronic diseases, resulting in a decrease in an accuracy of prediction, and an outstanding medical logic contradiction in prediction results of a plurality of diseases. Currently, very few clinical decision support systems are provided for medical examination using multi-label machine learning, and relevant research can only assist in a diagnosis of diseases at a current time node, but cannot perform prognostics on an occurrence of future chronic diseases of a medical examinee.

SUMMARY

In view of deficiencies of the prior art, an objective of the present invention is to provide a system for the prognostics of the chronic diseases after the medical examination based on the multi-label learning. Modules of the system aim at a multi-label learning model for a physical examination scenario, and fully extract time sequence information between a medical examination time point in existing medical data and an occurrence time of subsequent chronic diseases to complete a prediction of an occurrence of the chronic diseases in the next 1 to 5 years. The system can better tap a medical value which a single medical examination can bring, so that the public can have a better understanding of current and future personal medical conditions via the medical examination, and improve an actual effect of the medical examination on early awareness of the chronic diseases.

The objective of the present invention is realized through the following technical solutions: a system for the prognostics of the chronic diseases after the medical examination based on the multi-label learning includes a data acquisition module, a data preprocessing module, a basic predicting model constructing module, and a local predicting module.

The data acquisition module is configured to acquire physical examination data of a physical examination user. The physical examination data includes basic physiological indicators and routine assay indicators. The basic physiological indicators include a height, a weight, a blood pressure and other indicators that can be directly measured. The routine assay indicators include a blood routine, a urine routine and other indicators obtained through a sample assay. All the forgoing indicators of the physical examination user are expressed as a feature vector $X=[x_1, x_2, \ldots x_p]^T$. p is the total number of indicators. An occurrence time $t_0$ of a current medical examination is recorded. The earliest occurrence time data $T=[t_1, t_2, \ldots t_q]^T$ of a diagnosis of various chronic diseases (such as a diabetes, a hypertension, a coronary heart disease, a chronic kidney disease, or the like) from diagnosis data of the chronic diseases in the user's electronic medical record before and after the medical examination is extracted. q is the number of categories of the chronic diseases preset by the system. In the forgoing data, X, $t_0$ is a necessary data. Each of components in T is set as null when the diagnosis does not exist.

A processing process of the data preprocessing module is specifically as follows:

performing standardization processing $\phi_i$ on each of the components $x_i$ in X based on the component, so that a standard deviation of all data on this component is 1, and a mean value of all the data on this component is 0. A standardized feature vector is denoted as $X'=[x'^1, x'^2, \ldots x'^p]^T$;

$$x_i' = \phi_i(x_i) = \frac{(x_i - \lambda_i)}{\sigma_i}$$

where, $x_i'$ is a standardized data. $\lambda_i$ is the mean value of all the data on the component $x_i$. $\sigma_i$ is the standard deviation of all the data on the component $x_i$;

performing an exponential operation on T based on a base number $\alpha(0<\alpha<1)$ to generate a prognostic index vector $Y=[y_1, y_2, \ldots y_q]^T$:

$$y_i = y(t_i) = \begin{cases} \alpha^{(t_i - t_0)} & t_i > t_0 \\ 1 & t_i \le t_0 \\ 0 & t_i \text{ is null} \end{cases}$$

The basic predicting model constructing module is configured to construct a multi-label learning model for a physical examination scenario, and a constructing process is as follows:

(1) constructing a multilayer neural network, and completing data processing from input to output via the multilayer neural network, where, specific hyperparameters of the network include: the number K of layers of the network, the number $n_1, n_2, \ldots n_K$ of nodes in each of the layers of the network, and an activation function between two adjacent layers, where $n_1=p$, $n_K=q$; transfer weight matrixes between two adjacent layers are denoted as $W_1, W_2, \ldots W_{K-1}$; and an output value of the nodes of the last layer is denoted as a predicted prognostic index $C=[c_1, c_2, \ldots c_q]^T$;

(2) designing a loss function E, where, the loss function is a key definition that enables the model to adaptively learn an occurrence state and an occurrence sequence of various chronic diseases to perform prognostics of future chronic diseases of a medical examinee;

$$E = \frac{1}{N} \sum_{k=1}^{N} \sum_{i=0}^{2} \lambda_i^w \cdot E_i^k$$

The loss function can be regarded as a weighted mean value of three loss functions set for different objectives, where, N represents a data sample amount used in a single batch of gradient descent, and a superscript k of $E_i^k$ indicates that a component of the loss function is obtained by calculation of a k-th sample in the batch of gradient descent. $\lambda_i^w$ represents respective weight values of the three loss functions;

a) $E_0$ is a single-label loss function, which characterizes a difference between a predicted prognostic index $c_i$ and an actual prognostic index $y_i$ of disease prediction:

$$E_0 = -\frac{1}{q}\sum_i y_i \log c_i \text{ or } E_0 = \frac{1}{q}(y_i - c_i)^2$$

b) $E_1$ is an interval loss function, which characterizes a difference between a predicted prognostic index difference $\Delta c_{i,j}$ and an actual prognostic index difference $\Delta y_{i,j}$ of two different chronic diseases:

$$E_1 = \frac{1}{q(q-1)} \sum_{i \ne j} [(y_i - y_j) - (c_i - c_j)]^2 = \frac{1}{q(q-1)} \sum_{i \ne j} (\Delta y_{i,j} - \Delta c_{i,j})^2$$

c) $E_2$ is a ranking loss function, which characterizes a difference between a predicted occurrence order and an actual occurrence order of the two different chronic diseases:

$$E_2 = \frac{1}{q(q-1)} \sum_{i \ne j} e^{-(y_i - y_j)(c_i - c_j)} = \frac{1}{q(q-1)} \sum_{i \ne j} e^{-\Delta y_{i,j} \cdot \Delta c_{i,j}}$$

With this loss function, an actual occurrence time of the diseases, an occurrence logical relation between the diseases, and a time interval between the diseases can be considered during model training, so that an occurrence of a plurality of diseases in the future can be better predicted based on a single physical examination data.

(3) Learning parameters: according to the physical examination data of a sample medical institution, several models $M_1, M_2, \ldots M_L$ are constructed by matrix hyperparameter scanning (i.e., hyperparameters for scanning: the number K of the layers of the network, the number $n_2, \ldots n_{K-1}$ of nodes in middle layers of the network, and activation functions between two adjacent layers). Parameters of each of the models are learned based on a mini-batch gradient descent (MBGD). Optimal parameters are determined via k-fold cross validation. An optimal model is used as a basic predicting model $M_{best}$ for migration to other medical institutions. $M_{best}$ is solidified into the basic predicting model constructing module.

The local predicting module is arranged in a specific local medical institution and includes a local model training unit and a predicting unit.

The local model training unit obtains an optimal basic predicting model $M_{best}$ via the basic predicting model constructing module that is adjusted via real data of a sample medical institution. However, due to different testing instruments and methods used by different medical institutions, the parameters need to be adaptively adjusted based on specific physical examination data of the specific local medical institution to determine an local predicting model $M_{best}^H$ for the specific local medical institution;

The local model training unit receives the optimal basic predicting model $M_{best}$ provided by the basic predicting model constructing module, acquires the physical examination data X, $t_0$, T of the specific local medical institution via the data acquisition module, generates X', Y via the data preprocessing module, performs model training the same as a $M_{best}$ training method with model parameters of $M_{best}$ as initial parameters based on X', Y, and solidifies a trained local predicting model $M_{best}^H$ into the local predicting module after the parameters are converged.

The predicting unit performs the prognostics of the chronic diseases based on physical examination data of a new medical examinee according to the local predicting model $M_{best}^H$, outputs a predicted prognostic index $C=[c_1, c_2, \ldots c_q]^T$ of the occurrence of the plurality of chronic diseases, and then obtains a future expected occurrence time $t'_i$ of the corresponding chronic disease via an inverse function $t'_i = y^{-1}(c_i)$ of $y(t_i)$. For a disease whose occurrence time is greater than a cut-off time $t_{cutoff}$, a risk of occurrence of the diseases in a short term is considered to be low. A predicted occurrence time of the chronic diseases is fed back to the medical examinee via a natural language generation method, so that the medical examinee can understand high-risk diseases in the future, thereby providing a reference for a targeted adjustment of living habits and better prevention and treatment of high-incidence diseases.

Further, the medical institution stores the physical examination data as a .csv file locally. A selected sample medical institution generates an encapsulated basic predicting model $M_{best}$ from the physical examination data of the sample medical institution. The physical examination data of a local medical institution is sent to its local predicting module via an interface service, and the future expected occurrence time of the corresponding chronic diseases is returned via an interface response.

The beneficial effects of the present invention are as follows: the system of the present invention can extract an internal relation in a case of a concurrence of the chronic diseases with a multi-label learning method, which is more in line with a feature of high concurrency of the chronic diseases, and can better accurately predict an occurrence of the future chronic diseases. In addition, a complete set of solutions including data acquiring, data preprocessing, basic predicting model construction and local prediction output is completed.

DESCRIPTION OF EMBODIMENTS

The present invention is further described in detail below in conjunction with the drawings and specific embodiments.

Figure 1:
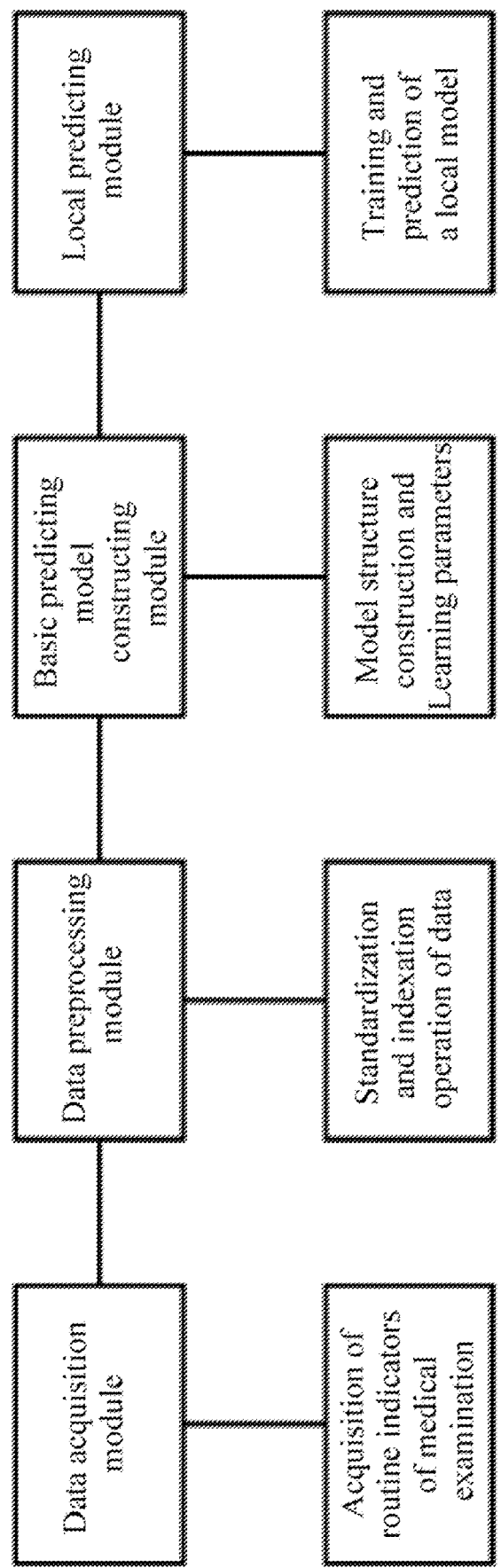
FIG. 1 is a schematic structural diagram of a system for the prognostics of the chronic diseases after the medical examination based on the multi-label learning.

As shown in FIG. 1, the present invention provides a system for the prognostics of the chronic diseases after the medical examination based on the multi-label learning. The system can provide prognostic information on an occurrence of chronic diseases including complications in the future based on physical examination data of a medical examinee at a current time node. An example of the implementation of this system is given below, but the system is not limited thereto:

The system includes a data acquisition module, a data preprocessing module, a basic predicting model constructing module, and a local predicting module.

The data acquisition module is configured to acquire physical examination data of a physical examination user. The physical examination data includes basic physiological indicators and routine assay indicators. The basic physiological indicators include a height, a weight, BMI, a systolic blood pressure, and a diastolic blood pressure. The routine assay indicators include a blood routine (total protein, albumin, globulin, an albumin/globulin ratio, alanine aminotransferase, aspartate aminotransferase, alkaline phosphatase, cholinesterase, total bile acid, total bilirubin, direct bilirubin, indirect bilirubin, adenylate deaminase, glutamyl transpeptidase, glomerular filtration rate, creatinine, urea, uric acid, bronostatin C, triglycerides, total cholesterol, high-density lipoprotein-C, low-density lipoprotein-C, very low-density lipoprotein-C, fasting blood glucose, potassium, sodium, chloride, total calcium, inorganic phosphorus, glyphosate dipeptide aminopeptidase, a-fucosidase), and a urine routine (urine protein, urine ketone bodies, urine glucose, urine sediment red blood cells, urine bilirubin, urine sediment white blood cells, urine sediment red blood cells, urobilinogen, uric acidity). All the forgoing indicators of the physical examination user are expressed as feature vectors $X = [x_1, x_2, \ldots x_p]^T$. $p = 46$ is the total number of indicators. An occurrence time $t_0$ of a current medical examination is recorded. The earliest occurrence time data $T = [t_1, t_2, \ldots t_q]^T$ of diagnosis of the chronic diseases (a diabetes, a hypertension, a hyperlipidemia, a hyperuricemia, a fatty liver, a coronary heart disease, and a chronic kidney disease) from diagnosis data of the chronic diseases in the user's electronic medical record before and after the medical examination is extracted. $q = 7$ is the number of categories of the chronic diseases preset by the system. In the forgoing data, X, $t_0$ is necessary data, and each of components in T is set to null when the diagnosis does not exist;

The data preprocessing module performs specifically the following:

performing standardization processing $\phi_i$ on each of the components $x_i$ in X based on the component, so that a standard deviation of all data on this component is 1, and a mean value of all the data on this component is 0. A standardized feature vector is denoted as $X' = [x'^1, x'^2, \ldots x'^p]^T$;

$$x'_i = \phi_i(x_i) = \frac{(x_i - \lambda_i)}{\sigma_i}$$

where, $x_i'$ is a standardized data. $\lambda_i$ is the mean value of all the data on the component $x_i$. $\sigma_i$ is the standard deviation of all the data on the component $x_i$;

performing an exponential operation on T based on a base number $\alpha (0 < \alpha < 1)$ to generate a prognostic index vector $Y = [y_1, y_2, \ldots y_q]^T$:

$$y_i = y(t_i) = \begin{cases} \alpha^{(t_i - t_0)} & t_i > t_0 \\ 1 & t_i \leq t_0 \\ 0 & t_i \text{ is null} \end{cases}$$

Figure 2:
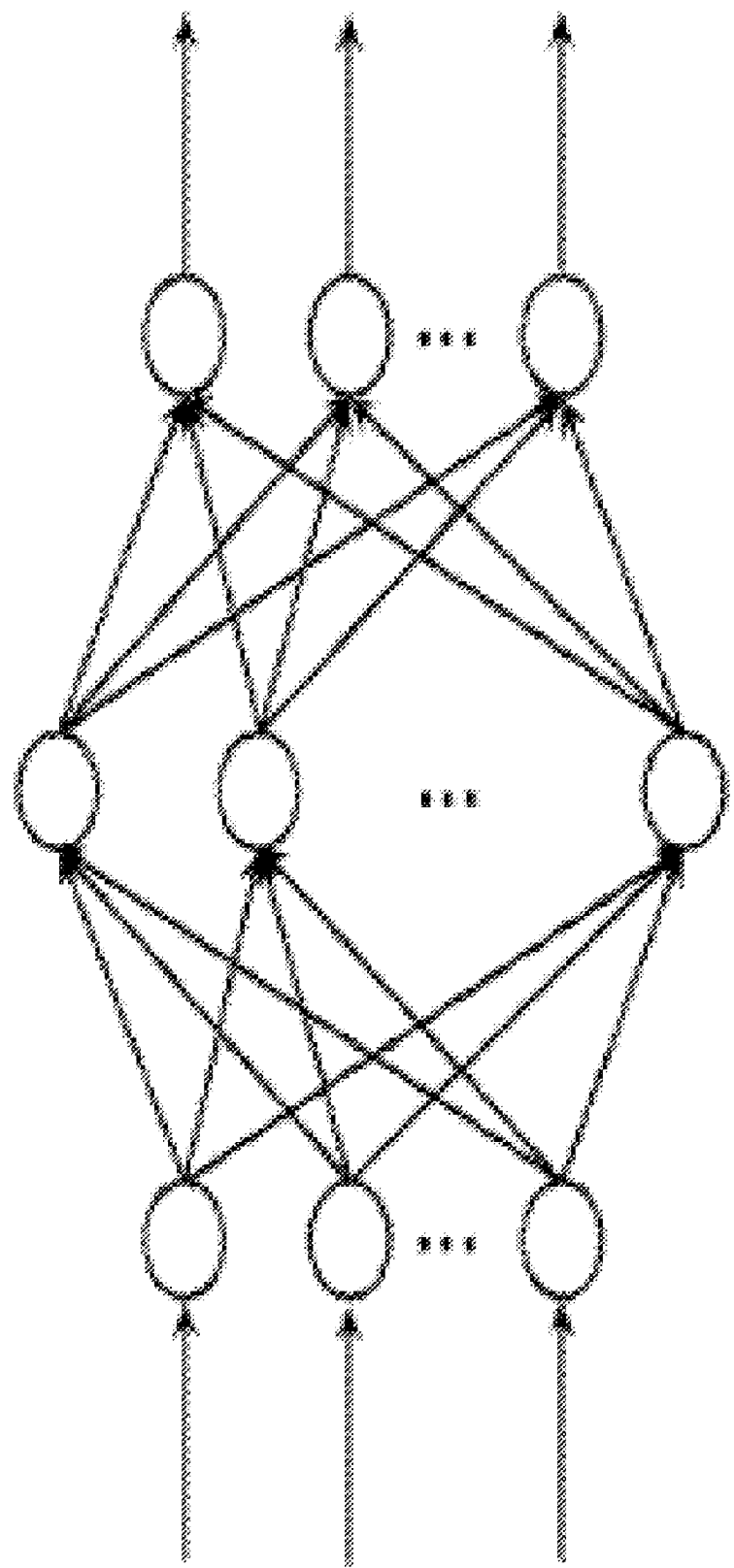
FIG. 2 is a structural diagram of a multilayer neural network.
Figure 3:
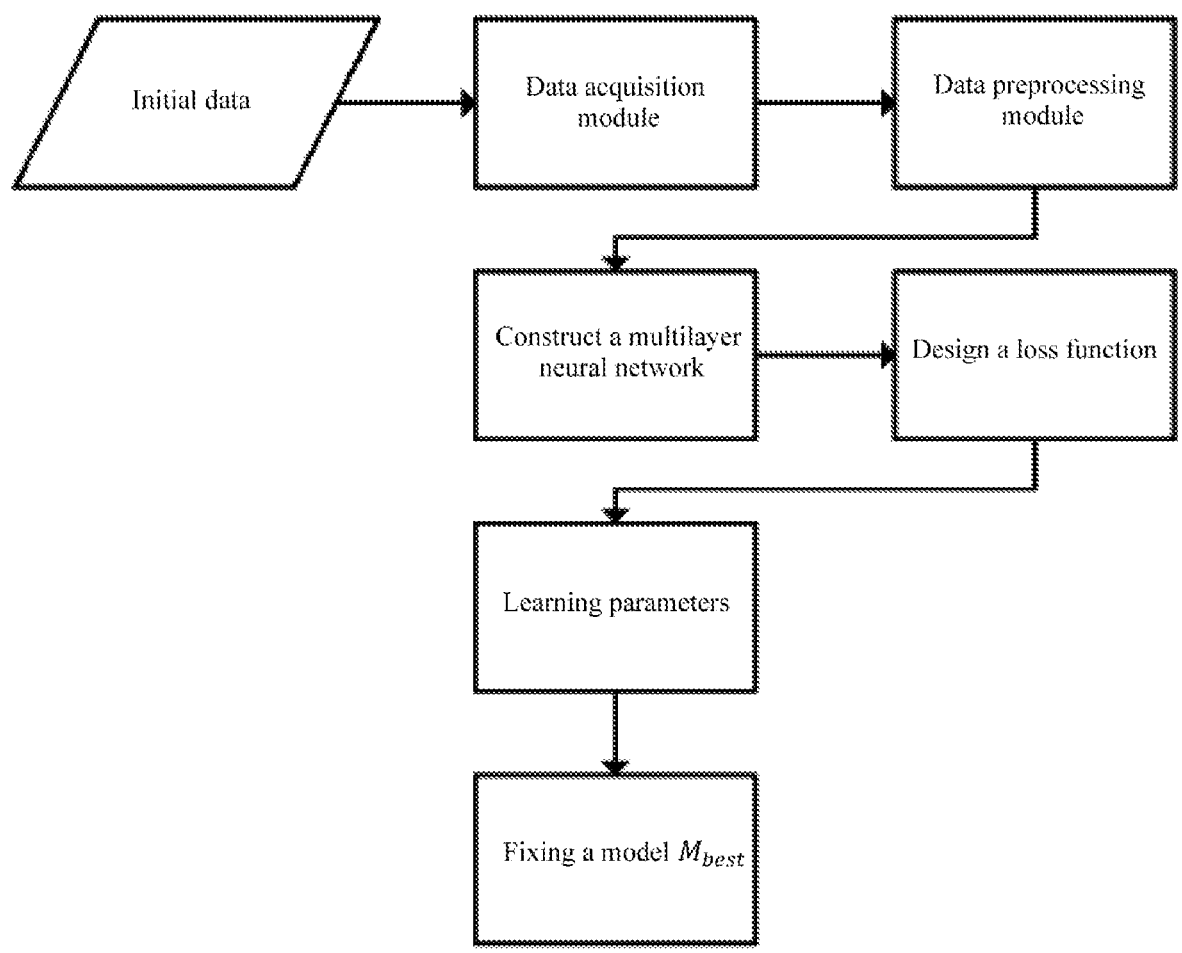
FIG. 3 is a schematic structural diagram of a basic predicting module constructing module.

The basic predicting model constructing module is configured to construct a multi-label learning model for a physical examination scenario. As shown in FIG. 3, a constructing process is as follows:

(1) constructing a multilayer neural network, and completing data processing from input to output via the multilayer neural network as shown in FIG. 2, where, specific hyperparameters of the network include: the number K of layers of the network, the number $n_1, n_2, \ldots n_K$ of nodes in each of the layers of the network, and an activation function between two adjacent layers, where $n_1 = p = 46$, $n_K = q = 7$; transfer weight matrixes between two adjacent layers are denoted as $W_1, W_2, \ldots W_{K-1}$; and an output value of the nodes of the last layer is denoted as a predicted prognostic index $C = [c_1, c_2, \ldots c_q]^T$; and (2) designing a loss function E, where, the loss function is a key definition that enables the model to adaptively learn an occurrence state and an occurrence sequence of various chronic diseases to perform prognostics of future chronic diseases of a medical examinee.

$$E = \frac{1}{N}\sum_{k=1}^{N}\sum_{i=0}^{2}\lambda_i^w \cdot E_i^k$$

The loss function can be regarded as a weighted mean value of three loss functions set for different objectives, where, N=20 represents a data sample amount used in a single batch of gradient descent, and a superscript k of $E_i^k$ represents that a component of the loss function is obtained by calculation of a k-th sample in the batch of gradient descent. $\lambda_i^w$ represents respective weight values of the three loss functions; $\lambda_0^w = \lambda_1^w = \lambda_2^w = 1$ is used in this embodiment.

a) $E_0$ is a single-label loss function, which characterizes a difference between a predicted prognostic index $c_i$ and an actual prognostic index $y_i$ of disease prediction:

$$E_0 = -\frac{1}{q}\sum_i y_i \log c_i \text{ or } E_0 = \frac{1}{q}(y_i - c_i)^2$$

b) $E_1$ is an interval loss function, which characterizes a difference between a predicted prognostic index difference $\lambda c_{i,j}$ and an actual prognostic index difference $\lambda y_{i,j}$ of two different chronic diseases:

$$E_1 = \frac{1}{q(q-1)}\sum_{i \ne j}[(y_i - y_j) - (c_i - c_j)]^2 = \frac{1}{q(q-1)}\sum_{i \ne j}(\Delta y_{i,j} - \Delta c_{i,j})^2$$

c) $E_2$ is a ranking loss function, which characterizes a difference between a predicted occurrence order and an actual occurrence order of the two different chronic diseases:

$$E_2 = \frac{1}{q(q-1)}\sum_{i \ne j}e^{-(y_i - y_j)(c_i - c_j)} = \frac{1}{q(q-1)}\sum_{i \ne j}e^{-\Delta y_{i,j} \cdot \Delta c_{i,j}}$$

With this loss function, an actual occurrence time of the diseases, an occurrence logical relation between the diseases, and a time interval between the diseases can be considered during model training, so that an occurrence of a plurality of diseases in the future can be better predicted based on a single physical examination data.

(3) Learning parameters: according to the physical examination data of a sample medical institution, several models $M_1, M_2, \ldots M_L$ are constructed by matrix hyperparameter scanning (i.e., hyperparameters for scanning: the number $K \in \{3, 4, 5, 6\}$ of the layers of the network, the number $n_2, \ldots n_{K-1} \in \{50, 30, 20, 10\}$ of nodes in middle layers of the network, and activation functions $\in \{\text{ReLU, sigmoid, Tanh}\}$ between two adjacent layers). Parameters of each of the models are learned based on a mini-batch gradient descent (MBGD). Optimal parameters are determined via 10-fold cross validation. An optimal model is used as a basic predicting model $M_{best}$ for migration to other medical institutions. $M_{best}$ is solidified into the basic predicting model constructing module.

Figure 4:
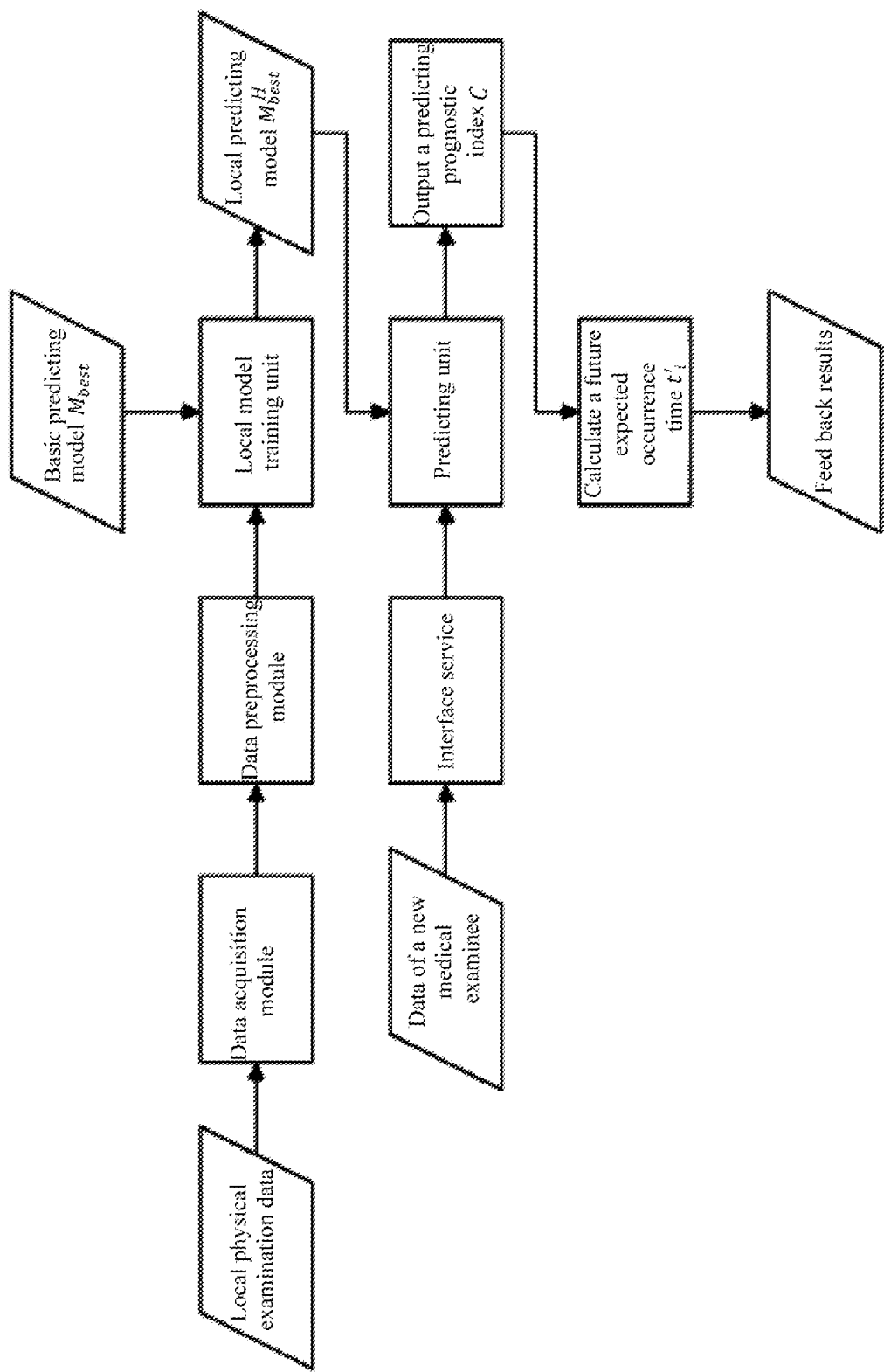
FIG. 4 is a schematic structural diagram of a local predicting module.

The local predicting module is arranged in a specific local medical institution and includes a local model training unit and a predicting unit as shown in FIG. 4.

The local model training unit obtains an optimal basic predicting model $M_{best}$ via the basic predicting model constructing module that is adjusted via real data of a sample medical institution. However, due to different testing instruments and methods used by different medical institutions, the parameters need to be adaptively adjusted based on specific physical examination data of the specific local medical institution to determine an local predicting model $M_{best}^H$ for the specific local medical institution.

The local model training unit receives the optimal basic predicting model $M_{best}$ provided by the basic predicting model constructing module, acquires the physical examination data X, $t_0$, T of the specific local medical institution via the data acquisition module, generates X', Y via the data preprocessing module, performs model training the same as a $M_{best}$ training method with model parameters of $M_{best}$ as initial parameters based on X', Y, and solidifies a trained local predicting model $M_{best}^H$ into the local predicting module after the parameters are converged.

The predicting unit performs the prognostics of the chronic diseases based on physical examination data of a new medical examinee according to the local predicting model $M_{best}^H$, outputs a predicted prognostic index C=[$c_1$, $c_2, \ldots c_q$]$^T$ of the occurrence of the plurality of chronic diseases, and then obtains a future expected occurrence time $t'_i$ of the corresponding chronic disease via an inverse function $t'_i = y^{-1}(c_i)$ of $y(t_i)$. For a disease whose occurrence time is greater than a cut-off time $t_{cutoff} = 5$ year, a risk of occurrence of the diseases in a short term is considered to be low. A predicted occurrence time of the chronic diseases is fed back to the medical examinee via a natural language generation method, so that the medical examinee can understand high-risk diseases in the future, thereby providing a reference for a targeted adjustment of living habits and better prevention and treatment of high-incidence diseases.

Further, the medical institution stores the physical examination data as a .csv file locally. A selected sample medical institution generates an encapsulated basic predicting model $M_{best}$ from the physical examination data of the sample medical institution. The physical examination data of a local medical institution is sent to its local predicting module via an interface service, and the future expected occurrence time of the corresponding chronic diseases is returned via an interface response.

The forgoing is only examples of implementation of the present invention, and is not used to limit the protection scope of the present invention. Any modification, equivalent replacement, improvement, or the like made without creative labor within the spirit and principle of the present invention are all included in the protection scope of the present invention.

What is claimed is:

1. A system for the prognostics of the chronic diseases after the medical examination based on the multi-label learning, comprising a data acquisition module, a data preprocessing module, a basic predicting model constructing module, and a local predicting module; wherein the data acquisition module is configured to acquire physical examination data of a physical examination user, the physical examination data comprises basic physiological indicators and routine assay indicators, all the forgoing indicators of the physical examination user are expressed as a feature vector X=[$x_1, x_2, \ldots x_p$]$^T$, p is the total number of indicators, an occurrence time $t_0$ of a current medical examination is recorded, the earliest occurrence time data T=[$t_1, t_2, \ldots t_q$]$^T$ of a diagnosis of various chronic diseases in diagnosis data in the chronic diseases in an electronic medical record of the physical examination user before and after the medical examination is extracted, q is the number of categories of the chronic diseases preset by the system, in the forgoing data, X, $t_0$ is necessary data, each of components in T is set as null when the diagnosis does not exist;

a processing process of the data preprocessing module is specifically as follows:

performing standardization processing $\phi_i$ on each component $x_i$ in X based on the component, so that a standard deviation of all data on the component is 1, and a mean value of all the data is 0, a standardized feature vector is denoted as $X'=[x'_1, x'_2, \ldots x'_p]^T$;

$$x'_i = \phi_i(x_i) = \frac{(x_i - \lambda_i)}{\sigma_i}$$

where, $x_i'$ is a standardized data, $\lambda_i$ is the mean value of all the data on the component $x_i$, $\sigma_i$ is the standard deviation of all the data on the component $x_i$;

performing an exponential operation on T based on a base number $\alpha(0<\alpha<1)$ to generate a prognostic index vector $Y=[y_1, y_2, \ldots y_q]^T$:

$$y_i = y(t_i) = \begin{cases} \alpha^{(t_i - t_0)} & t_i > t_0 \\ 1 & t_i \leq t_0 \\ 0 & t_i \text{ is null} \end{cases}$$

the basic predicting model constructing module is configured to construct a multi-label learning model for a physical examination scenario, and a constructing process is as follows:

(1) constructing a multilayer neural network, and completing data processing from input to output via the multilayer neural network, wherein specific hyperparameters of the multilayer neural network comprise: a number K of layers of the multilayer neural network, a number $n_1, n_2, \ldots n_K$ of nodes in each of the layers of the multilayer neural network, and an activation function between two adjacent layers, where $n_1=p$, $n_K=q$; transfer weight matrixes between two adjacent layers are denoted as $W_1, W_2, \ldots W_{K-1}$; and an output value of the nodes of the last layer is denoted as a predicted prognostic index $C=[c_1, c_2, \ldots c_q]^T$;

(2) designing a loss function E:

$$E = \frac{1}{N} \sum_{k=1}^{N} \sum_{i=0}^{2} \lambda_i^w \cdot E_i^k$$

the loss function can be regarded as a weighted mean value of three loss functions set for different objectives, wherein N represents a data sample amount used in a single batch of gradient descent, and a superscript k of $E_i^k$ represents that a component of the loss function is obtained by calculation of a k-th sample in the batch of gradient descent, $\lambda_i^w$ represents respective weight values of the three loss functions;

a) $E_0$ is a single-label loss function, which characterizes a difference between a predicted prognostic index $c_i$ and an actual prognostic index $y_i$ of disease prediction:

$$E_0 = -\frac{1}{q}\sum_i y_i \log c_i \text{ or } E_0 = \frac{1}{q}(y_i - c_i)^2$$

b) $E_1$ is an interval loss function, which characterizes a difference between a predicted prognostic index difference $\Delta c_{i,j}$ and an actual prognostic index difference $\Delta y_{i,j}$ of two different chronic diseases:

$$E_1 = \frac{1}{q(q-1)}\sum_{i \neq j}[(y_i - y_j) - (c_i - c_j)]^2 = \frac{1}{q(q-1)}\sum_{i \neq j}(\Delta y_{i,j} - \Delta c_{i,j})^2$$

c) $E_2$ is a ranking loss function, which characterizes a difference between a predicted occurrence order and an actual occurrence order of the two different chronic diseases:

$$E_2 = \frac{1}{q(q-1)}\sum_{i \neq j}e^{-(y_i - y_j)(c_i - c_j)} = \frac{1}{q(q-1)}\sum_{i \neq j}e^{-\Delta y_{i,j} \cdot \Delta c_{i,j}}$$

(3) learning parameters: according to the physical examination data of a sample medical institution, several models $M_1, M_2, \ldots M_L$ are constructed by matrix hyperparameter scanning, parameters of each of the models are learned based on a mini-batch gradient descent (MBGD), optimal parameters are determined via k-fold cross validation, an optimal model is used as a basic predicting model $M_{best}$ for migration to other medical institutions, $M_{best}$ is solidified into the basic predicting model constructing module;

the local predicting module is arranged in a specific local medical institution and comprises a local model training unit and a predicting unit;

the local model training unit receives an optimal basic predicting model $M_{best}$ provided by the basic predicting model constructing module, acquires the physical examination data X, $t_0$, T of the specific local medical institution via the data acquisition module, generates X', Y via the data preprocessing module, performs model training the same as a $M_{best}$ training method with model parameters of $M_{best}$ as initial parameters based on X', Y, and solidifies a trained local predicting model $M_{best}^H$ into the local predicting module after the parameters are converged;

the predicting unit performs the prognostics of the chronic diseases based on physical examination data of a new medical examinee according to the local predicting model $M_{best}^H$, outputs a predicted prognostic index $C=[c_1, c_2, \ldots c_q]^T$ of the occurrence of the plurality of chronic diseases, and then obtains a future expected occurrence time $t'_i$ of the corresponding chronic disease via an inverse function $t'_i = y^{-1}(c_i)$ of $y(t_i)$.

2. The system for the prognostics of the chronic diseases after the medical examination based on the multi-label learning according to claim 1, wherein the medical institution stores the physical examination data as a .csv file locally; a selected sample medical institution generates an encapsulated basic predicting model $M_{best}$ from the physical examination data of the sample medical institution; the physical examination data of a local medical institution is sent to its local predicting module via an interface service, and the future expected time of the occurrence of the corresponding chronic diseases is returned via an interface response.

\* \* \* \* \*